United States Patent
Salem et al.

(10) Patent No.: US 9,468,908 B2
(45) Date of Patent: Oct. 18, 2016

(54) REDUCTION CATALYSTS

(71) Applicant: Rennovia Inc., Menlo Park, CA (US)

(72) Inventors: George Fredrick Salem, Los Altos, CA (US); Guang Zhu, Union City, CA (US); Alfred Gerhard Hagemeyer, Sunnyvale, CA (US); Eric L. Dias, Belmont, CA (US)

(73) Assignee: Renovia Inc., Santa Clara, CA (US)

( * ) Notice: Subject to any disclaimer, the term of this patent is extended or adjusted under 35 U.S.C. 154(b) by 412 days.

(21) Appl. No.: 13/894,351

(22) Filed: May 14, 2013

(65) Prior Publication Data

US 2013/0310605 A1 Nov. 21, 2013

Related U.S. Application Data (60) Provisional application No. 61/647,464, filed on May 15, 2012.

(51) Int. Cl.
*C07C 51/36* (2006.01)
*B01J 23/00* (2006.01)
(Continued)

(52) U.S. Cl.
CPC ............. *B01J 23/464* (2013.01); *B01J 21/063* (2013.01); *B01J 21/066* (2013.01); *B01J 23/40* (2013.01);
(Continued)

(58) Field of Classification Search
CPC ........ B01J 21/066; B01J 23/40; B01J 23/42; B01J 23/44; B01J 23/46; B01J 23/63; B01J 23/6525; B01J 23/6527; C07C 51/36
USPC ........ 502/302–304, 308, 326, 332–334, 339, 502/349; 562/592
See application file for complete search history.

(56) References Cited

U.S. PATENT DOCUMENTS 4,400,468 A 8/1983 Faber
5,487,987 A 1/1996 Frost et al.
(Continued)

FOREIGN PATENT DOCUMENTS

EP 1839746 A1 10/2007
JP 53-144506 A 12/1978
(Continued)

OTHER PUBLICATIONS

International Search Report and Written Opinion received for PCT Patent Application No. PCT/US2013/040997, mailed on Oct. 11, 2013, 8 pages.
(Continued)

*Primary Examiner* — Cam N. Nguyen
(74) *Attorney, Agent, or Firm* — Senniger Powers LLP (57) ABSTRACT

Disclosed are catalysts comprised of platinum and rhodium on a support selected from the group of zirconia, stabilized (doped) zirconia, zirconia-metal oxide composites, and mixtures thereof, wherein the outer surfaces of the support are selected from the group of zirconia, stabilized zirconia, and mixtures thereof. More particularly, the supported catalysts comprise platinum and rhodium, wherein the molar ratio of platinum to rhodium is in the range of about 3:1 to about 1:2. The average pore diameter of the catalyst supports is in the range of about 5 nm to about 70 nm and the surface area is in the range of about 15 m²/g to about 200 m²/g. Also disclosed are methods for the hydrodeoxygenation of carboxylic acids, mono- and/or di-lactones thereof having at least one hydroxyl group on the backbone thereof to corresponding acids where the backbone hydroxyl group has been reduced in the presence of the catalyst.

47 Claims, 2 Drawing Sheets

(51) Int. Cl.
  B01J 23/10        (2006.01)
  B01J 23/40        (2006.01)
  B01J 23/42        (2006.01)
  B01J 23/44        (2006.01)
  B01J 23/56        (2006.01)
  B01J 23/46        (2006.01)
  B01J 37/02        (2006.01)
  B01J 21/06        (2006.01)
  B01J 35/10        (2006.01)
  C07C 51/377       (2006.01)
  B01J 21/18        (2006.01)
  B01J 23/58        (2006.01)
  B01J 29/04        (2006.01)

(52) U.S. Cl.
  CPC ......... *B01J 35/1014* (2013.01); *B01J 35/1061* (2013.01); *B01J 35/1066* (2013.01); *B01J 37/024* (2013.01); *B01J 37/0205* (2013.01); *C07C 51/377* (2013.01); *B01J 21/18* (2013.01); *B01J 23/58* (2013.01); *B01J 29/04* (2013.01)

(56) References Cited

U.S. PATENT DOCUMENTS

| | | | |
|---|---|---|---|
| 5,516,960 A | 5/1996 | Robinson | |
| 5,945,369 A * | 8/1999 | Kimura | B01D 53/945 502/304 |
| 7,022,644 B2 * | 4/2006 | Foong | B01D 53/945 502/302 |
| 7,220,701 B2 * | 5/2007 | Lowe | B01J 23/62 502/325 |
| 8,273,681 B2 * | 9/2012 | Naito | B01D 53/945 502/302 |
| 8,569,201 B2 * | 10/2013 | Naito | B01D 53/945 502/302 |
| 2002/0160912 A1 * | 10/2002 | Morikawa | B01D 53/944 502/303 |
| 2007/0215484 A1 | 9/2007 | Peterson et al. | |
| 2007/0225159 A1 * | 9/2007 | Ibe | B01D 53/945 502/304 |
| 2009/0272943 A1 * | 11/2009 | Chartier | B01J 23/63 252/373 |
| 2010/0317823 A1 | 12/2010 | Boussie et al. | |
| 2013/0158255 A1 | 6/2013 | Archer et al. | |

FOREIGN PATENT DOCUMENTS

| | | |
|---|---|---|
| WO | WO2010/144862 * | 12/2010 |
| WO | 2011/109051 A1 | 9/2011 |

OTHER PUBLICATIONS

Barrett et al., "The Determination of Pore Volume and Area Distributions in Porous Substances. I. Computations from Nitrogen Isotherms", Journal of the American Chemical Society, vol. 73, Jan. 1951, pp. 373-380.

Brunauer et al., "Adsorption of Gases in Multimolecular Layers", Journal of the American Chemical Society, vol. 60, Feb. 1938, pp. 309-319.

Gehret et al., "Convenient Large-Scale Synthesis of D-Glucaro-1,4:6,3-dilactone", The Journal of Organic Chemistry. vol. 74, No. 21, 2009, pp. 8373-8376.

Niu et al., "Benzene-Free Synthesis of Adipic Acid", Biotechnology Progress, vol. 18, Issue 2, 2002, pp. 201-211.

"Standard Test Method for Determination of Nitrogen Adsorption and Desorption Isotherms of Catalysts and Catalyst Carriers by Static Volumetric Measurements", Book of Standards vol. 05.05, Active Standard ASTM D4222, 2008.

"Standard Test Method for Surface Area of Catalysts and Catalyst Carriers", Book of Standards vol. 05.05, Active Standard ASTM D3663, 2008.

* cited by examiner

REDUCTION CATALYSTS

CROSS-REFERENCE TO RELATED APPLICATION

This application claims the benefit under 35 U.S.C. 119(e) of U.S. Provisional Application No. 61/647,464, filed on May 15, 2012, the disclosure of which is hereby incorporated by reference in its entirety.

BACKGROUND

I. Field

The present invention relates generally to heterogeneous catalysts comprised of platinum and rhodium on a support at least the outer surfaces of which are selected from the group consisting of zirconia, stabilized (doped) zirconia, zirconia-metal oxide composites and mixtures thereof. The catalysts of the present invention are particularly useful for the selective reduction of compositions of the general formula ROOC(CX)$_y$COOR, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof, to dicarboxylic acids and derivatives thereof. More particularly, the present invention is directed to catalysts for the selective hydrodeoxygenation of such compositions to dicarboxylic acids and/or derivatives thereof, especially adipic acid and/or derivatives thereof.

II. Related Art

Crude oil is currently the source of most commodity and specialty organic chemicals. Many of these chemicals are employed in the manufacture of polymers and other materials. Examples include ethylene, propylene, styrene, bisphenol A, terephthalic acid, adipic acid, caprolactam, hexamethylene diamine, adiponitrile, caprolactone, acrylic acid, acrylonitrile, 1,6-hexanediol, 1,3-propanediol, and others. Crude oil is first refined into hydrocarbon intermediates such as ethylene, propylene, benzene, and cyclohexane. These hydrocarbon intermediates are then typically selectively oxidized using various processes to produce the desired chemical. For example, crude oil is refined into cyclohexane which is then selectively oxidized to "KA oil" which is then further oxidized for the production of adipic acid, an important industrial monomer used for the production of nylon 6,6. Many known processes are employed industrially to produce these petrochemicals from precursors found in crude oil. For example, see *Ullmann's Encyclopedia of Industrial Chemistry*, Wiley 2009 (7th edition), which is incorporated herein by reference.

For many years there has been an interest in using biorenewable materials as a feedstock to replace or supplement crude oil. See, for example, Klass, Biomass for Renewable Energy, Fuels, and Chemicals, Academic Press, 1998, which is incorporated herein by reference. Moreover, there have been efforts to produce adipic acid from renewable resources using processes involving a combination of biocatalytic and chemocatalytic processes. See, for example, "Benzene-Free Synthesis of Adipic Acid", Frost et al. Biotechnol. Prog. 2002, Vol. 18, pp. 201-211, and U.S. Pat. Nos. 4,400,468, and 5,487,987.

One of the major challenges for converting biorenewable resources such as carbohydrates (e.g. glucose derived from starch, cellulose or sucrose) to commodity and specialty chemicals is the selective removal of oxygen atoms from the carbohydrate. Approaches are known for converting carbon-oxygen single bonds to carbon-hydrogen bonds. See, for example: U.S. Pat. No. 5,516,960; U.S. Patent App. Pub. US2007/0215484 and Japanese Patent No. 78,144,506. However, each of these known approaches suffers from various limitations and we believe that, currently, none of such methods are used industrially for the manufacture of specialty or industrial chemicals.

There remains a need for new, industrially viable catalysts for the selective and commercially-meaningful conversion of carbon-oxygen single bonds to carbon-hydrogen bonds, especially as applied in connection with the production of chemicals from hydroxyl-containing, dicarboxylate substrates (e.g., aldaric acids), and especially for the production of chemicals from polyhydroxyl-containing dicarboxylate substrates (e.g., glucaric acid) to important chemicals such as adipic acid.

SUMMARY

The present invention is directed to catalyst compositions comprising platinum and rhodium and a support at least the exposed surfaces of which are selected from the group of zirconia, stabilized (doped) zirconia, zirconia-metal oxide composites and mixtures thereof, wherein the molar ratio of platinum to rhodium on the support is in the range of from about 3:1 to about 1:2 and the total weight percent of platinum and rhodium is less than about 10 wt %. In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 70 nm. In some embodiments, the average pore diameter of the support is in the range of from about 5 nm to about 40 nm. In some embodiments, the surface area of the support is in the range of between about 15 m$^2$/g and about 200 m$^2$/g. In some embodiments, the surface area of the support is in the range of between about 15 m$^2$/g and about 125 m$^2$/g. In some embodiments, the surface area of the support is in the range of between about 15 m$^2$/g and about 60 m$^2$/g. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, platinum is present in an amount up to about 1.4 wt %. In some embodiments, rhodium is present in an amount up to about 0.8 wt %. In some embodiments, the total amount of platinum and rhodium present is equal to or less than about 4 wt %; in other embodiments, the total amount is equal to or less than about 2 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 μm.

The present invention is also directed to heterogeneous catalyst compositions useful for the selective hydrodeoxygenation of compositions of the general formula ROOC(CX)$_y$COOR, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof, to dicarboxylic acids and derivatives thereof wherein the catalyst comprises platinum and rhodium and a support selected from the group of zirconia, stabilized (doped) zirconia, zirconia-metal oxide composites and mixtures thereof, the molar ratio of platinum to rhodium on the support is in the range of from about 3:1 to about 1:2 and the total weight percent of platinum and rhodium is less than about 4 wt % (of the total catalyst weight). In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 70 nm. In some embodiments, the average pore diameter of the support is in the range of from about 5 nm to about 40 nm. In some embodiments, the surface area of the support is in the range of between about 15 m$^2$/g and about 200 m$^2$/g. In some embodiments, the surface area of the support is in the range of between about 15 m$^2$/g and about 125 m$^2$/g. In some embodiments, the surface area of the support is in the range of between about 15 m$^2$/g and about 60 m$^2$/g. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, platinum is present in an amount up to about 1.4 wt %. In some embodiments, rhodium is present in an amount up to about 0.8 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 μm.

The present invention is further directed to selective hydrodeoxygenation catalysts comprising platinum and rhodium and a support at least the exposed surfaces of which are selected from the group of zirconia, stabilized (doped) zirconia, zirconia-metal oxide composites, and mixtures thereof, wherein the molar ratio of platinum to rhodium on the support is in the range of from about 3:1 to about 1:2, the total weight percent of platinum and rhodium is less than about 10 wt %, and the average pore diameter of the catalyst is in the range of from about 5 nm to about 70 nm. In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 40 nm. In some embodiments, the surface area of the support is in the range of between about 15 m$^2$/g and about 200 m$^2$/g. In some embodiments, the surface area of the support is in the range of between about 15 m$^2$/g and about 125 m$^2$/g. In some embodiments, the surface area of the support is in the range of between about 15 m$^2$/g and about 60 m$^2$/g. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, platinum is present in an amount up to about 1.4 wt %. In some embodiments, rhodium is present in an amount up to about 0.8 wt %. In some embodiments, the total amount of platinum and rhodium present is equal to or less than about 4 wt %; in other embodiments, the total amount is equal to or less than about 2 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 μm.

Additionally, the present invention is directed to catalysts comprising platinum and rhodium and a support at least the outer surfaces of which are selected from the group consisting of zirconia, stabilized (doped) zirconia, zirconia-metal oxide composites and mixtures thereof, wherein the molar ratio of platinum to rhodium on the support is in the range of from about 3:1 to about 1:2, the total weight percent of platinum and rhodium is in the range of about 0.2 wt % to about 4 wt %, and the surface area of the catalyst is equal to or less than about 60 m$^2$/g. In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 70 nm. In some embodiments, the average pore diameter of the support is in the range of from about 5 nm to about 40 nm. In some embodiments, the surface area of the support is in the range of between about 15 m$^2$/g and about 60 m$^2$/g. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, platinum is present in an amount up to about 1.4 wt %. In some embodiments, rhodium is present in an amount up to about 0.8 wt %. In some embodiments, the total amount of platinum and rhodium present is in the range of from about 0.2 wt % to about 2 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 µm.

The present invention is also directed to catalysts comprising platinum and rhodium and a support at least the outer surfaces of which are selected from the group consisting of zirconia, stabilized (doped) zirconia, zirconia-metal oxide composites and mixtures thereof, wherein the molar ratio of platinum to rhodium on the support is in the range of from about 3:1 to about 1:2, and the average pore diameter of the support is in the range of from about 5 nm to about 70 nm. In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 40 nm. In some embodiments, the surface area of the support is in the range of between about 15 $m^2/g$ and about 200 $m^2/g$. In some embodiments, the surface area of the support is in the range of between about 15 $m^2/g$ and about 125 $m^2/g$. In some embodiments, the surface area of the support is in the range of between about 15 $m^2/g$ and about 60 $m^2/g$. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, the total amount of platinum and rhodium present is equal to or less than about 2 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 µm.

The present invention is also directed to processes for preparing adipic acid or derivatives thereof comprising reacting a substrate comprising material of the formula ROOC(CX)$_y$COOR, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof, with hydrogen in the presence of a catalyst comprising platinum and rhodium and a support at least the outer surfaces of which support are selected from the group consisting of zirconia, stabilized (doped) zirconia, zirconia-metal oxide composites and mixtures thereof, wherein the molar ratio of platinum to rhodium is in the range of from about 3:1 to about 1:2, to convert the substrate to adipic acid and/or derivative thereof. In some embodiments, at least a portion of the platinum and rhodium are impregnated into the support so as to form a metal-impregnated outer shell surrounding a core of essentially un-impregnated support material. In some embodiments, the molar ratio of platinum to rhodium is in the range of about 3:1 to about 1:1. In some embodiments, the average pore diameter of the support is in the range of from about 5 nm to about 70 nm. In some embodiments, the average pore diameter of the support is in the range of from about 5 nm to about 40 nm. In some embodiments, the surface area of the support is in the range of between about 15 $m^2/g$ and about 200 $m^2/g$. In some embodiments, the surface area of the support is in the range of between about 15 $m^2/g$ and about 125 $m^2/g$. In some embodiments, the surface area of the support is in the range of between about 15 $m^2/g$ and about 60 $m^2/g$. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, the total amount of platinum and rhodium present is equal to or less than about 10 wt %. In other embodiments, the total amount of platinum and rhodium present is equal to or less than about 4 wt %. In some embodiments, the total amount of platinum and rhodium present is equal to or less than about 2 wt %. In some embodiments, the total amount of platinum and rhodium present is in the range of from about 0.2 wt % to about 1.5 wt %.

The present invention is also directed to catalysts comprising platinum and rhodium and a support at least the outer surfaces of which support are selected from the group consisting of zirconia and stabilized zirconia, wherein the molar ratio of platinum to rhodium in the range of from about 3:1 to about 1:1, the average pore diameter of the support is in the range of from about 5 nm to about 70 nm and the surface area of the support is in the range of between about 15 $m^2/g$ and about 125 $m^2/g$. In some embodiments, at least a portion of the platinum and rhodium are impregnated into the support so as to form a metal-impregnated outer shell surrounding a core of essentially un-impregnated support material. In some embodiments, the average pore diameter of the support is in the range of from about 5 nm to about 40 nm. In some embodiments, the surface area of the support is in the range of between about 15 $m^2/g$ and about 60 $m^2/g$. In some embodiments, at least a portion of the platinum is present as Pt(0). In some embodiments, at least a portion of the rhodium is present as Rh(0). In some embodiments, the particle sizes of the metals are in the range of from about 2 nm to about 30 nm. In some embodiments, the particle sizes of the metals are in the range of from about 2 nm to about 20 nm. In some embodiments, the particle sizes of the metals are in the range of from about 2 nm to about 12 nm. In some embodiments, platinum is present in an amount up to about 1.4 wt %. In some embodiments, rhodium is present in an amount up to about 0.8 wt %. In some embodiments, the total amount of platinum and rhodium present is equal to or less than about 10 wt %. In some embodiments, the total amount of platinum and rhodium present is equal to or less than about 4 wt %. In some embodiments, the total amount of platinum and rhodium present is equal to or less than about 2 wt %. In some embodiments, the total amount of platinum and rhodium present is in the range of from about 0.2 wt % to about 1.5 wt %. In some embodiments, the catalyst further comprises a metal selected from the group of palladium, molybdenum and tungsten. In some embodiments, the catalyst is a shell type catalyst the outer surfaces of which are impregnated with the metals so as to create a metal-impregnated outer shell having a thickness equal to or less than about 150 μm.

The present invention is also directed to processes for producing an adipic acid product comprising reacting, in the presence of a catalyst comprising platinum and rhodium and a support at least the outer surfaces of which are selected from the group comprising zirconia, stabilized (doped) zirconia, zirconia-metal oxide composites, and mixtures thereof, wherein the molar ratio of platinum to rhodium is in the range of from about 3:1 to about 1:2 and the total weight percent of platinum and rhodium is equal to or less than about 10 wt % (of the total catalyst weight), with a substrate of the general formula $ROOC(CX)_y COOR$, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof under conditions to produce adipic acid product at a yield of at least 80%.

Other objects and features will become apparent and/or will be pointed out hereinafter.

DETAILED DESCRIPTION

In accordance with the present invention, applicants disclose heterogeneous catalysts comprised of platinum and rhodium on a support at least the outer surfaces of which are zirconia, stabilized (doped) zirconia, zirconia-metal oxide composites or mixtures thereof.

The heterogeneous catalysts of the present invention are useful generally for selective hydrodeoxygenation. More particularly, the catalysts of the present invention are useful in the selective hydrodeoxygenation of compositions of the general formula $ROOC(CX)_y COOR$, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof, to the corresponding dicarboxylic acids and derivative thereof of the general formula $ROOC(CH)_y COOR$, wherein "y" is at least 2 and up to about 10, preferably between about 2 and 4, and each "R" is, independently, selected from the group of salt-forming ions, hydrogen and hydrocarbyl or substituted hydrocarbyl or a mono- or di-lactone thereof.

The catalysts of the present invention are heterogeneous, solid-phase catalysts. The catalysts of the present invention comprise metals on at least the external surfaces (the "exposed surfaces") of a support at least the outer surfaces of which are selected from the group of zirconia, stabilized (doped) zirconia, zirconia(or stabilized zirconia)-metal oxide composites and mixtures thereof. In various embodiments, the supports consist essentially of zirconia or stabilized (doped) zirconia. A zirconia support means a support comprised of zirconia and no more than about 5 wt % of other materials, more typically less than about 2 wt %, not intentionally added to perform a specific function. Typically, these "trace" materials are hafnium, silica and/or titania. Zirconia exists in one or more crystalline phases: as essentially monoclinic, essentially tetragonal, monoclinic with a small fraction of tetragonal, or tetragonal with a small fraction of monoclinic. Stabilized zirconia (also referred as "doped" zirconia) is zirconia in combination with one or more metal oxides intentionally added to stabilize one or more of the phases of which the zirconia may exist, and typically the addition(s) is(are) present to stabilize the tetragonal phase of zirconia. Dopants used to stabilize zirconia can comprise between about 1 wt % and about 40 wt % of the total weight of the stabilized material, but more typically comprise less than about 20 wt % of the total weight of the stabilized material. Typical dopants/stabilizers include silica, titania, lanthana, yttria, ceria, tungsten, molybdenum, lanthanides, sulfate, and mixtures thereof. Preferred dopants are tungsten, molybdenum and silica. Zirconia (or stabilized-zirconia)-metal oxide composites are shell and core composites wherein the zirconia (or stabilized zirconia) form the shell of the support and another metal oxide (or different zirconia or stabilized zirconia) forms the core of the support. Useful core materials, in addition to zirconia or stabilized zirconia, include silicas or silicates, titanias and aluminas. Those of ordinary skill in the art are readily capable of producing useful composite catalyst supports.

The overall shape of the catalyst support is not critical. The catalysts can be in the form of, for example, spheres, beads, cylinders, lobed shapes (for example, bi-, tri-, star-), holed (for example, rings, cored beads, spheres, cylinders, or lobe shapes), and the metal distribution on the surface of the support can be uniform or non-uniform. Typically, the metal is distributed such that it forms a metal-impregnated outer shell having a thickness in the range of about 30 μm to about 150 μm, and more typically the thickness of the metal-impregnated outer shell is equal to or less than about 100 μm.

We have discovered that the catalysts of the present invention are particularly effective as hydrodeoxygenation catalysts in part because the surface area of the supports thereof are in the range of between about 15 $m^2/g$ and about 200 $m^2/g$, preferably are in the range of between about 15 $m^2/g$ and about 125 $m^2/g$, and more preferably equal to or less than about 60 $m^2/g$. In various embodiments, the surface area of the supports are in the range of from about 15 $m^2/g$ to about 60 $m^2/g$. Further, controlling the average pore diameters of the support also advantageously, and unexpectedly, benefits the performance of the catalysts of the present invention; to that end, the average pore diameters of the supports of the present invention are in the range of at least about 5 nanometer (nm) to about 70 nanometer (nm), preferably in the range of from about 5 nm to about 40 nm, and exhibit a monomodal or multimodal pore size distribution. The pore volume of the supports of the catalysts of the present invention are in the range of from about 0.1 ml/g to about 1.0 ml/g, and more typically are less than or equal to about 0.5 ml/g. Average pore diameters and pore volumes are determined in accordance with the procedures described in E. P. Barrett, L. G. Joyner, P. P. Halenda, J. Am. Chem. Soc. 1951, 73, 373-380, and ASTM D4222-03(2008) Standard Test Method for Determination of Nitrogen Adsorption and Desorption Isotherms of Catalysts and Catalyst Carriers by Static Volumetric Measurements. Surface area is determined in accordance with the methods described in S. Brunauer, P. H. Emmett, E. Teller, J. Am. Chem. Soc. 1938, 60, 309-331, and ASTM D3663-03(2008) Standard Test Method for Surface Area of Catalysts and Catalyst Carriers.

The catalysts of the present invention may be produced by deposition procedures known in the art including, but not limited to, incipient wetness, ion-exchange and deposition-precipitation and absorption from excess solution (volume higher than ion exchange or incipient wetness), physical vapor deposition, chemical vapor deposition, solution coating or wash coating. In various embodiments, a uniform dispersion can be effected by forming a heterogeneous slurry or suspension of the support in combination with solubilized metal complexes. In certain embodiments, the supports may be initially dispersed in a liquid such as water; thereafter, in such embodiments, the solubilized metal complexes may be added to the slurry containing the support. The heterogeneous mixture of solid and liquids can then be stirred, mixed and/or shaken or fluidized to enhance the uniformity of dispersion of the catalyst components which, in turn, enables the more uniform deposition of metals on the surface of the support upon removal of the liquids and undertaking additional treatments as may be needed to produce the catalyst (and more fully described hereinafter). The opposite order of addition (i.e. adding the support to the metal solution) is also possible.

The platinum is typically added to the support as a solution of a soluble precursor or as a colloid. Platinum-containing compounds useful in the present invention include nitrogen containing compounds such as platinum (II)dinitrate, platinum (IV) nitrate, platinum oxynitrate, tetraamineplatinum (II) nitrate, tetraamineplatinum (II) hydrogenphosphate, tetraamineplatinum (II) hydrogencarbonate, tetraamineplatinum (II) hydroxide, ethanolaminehexahydroxyplatinate (IV) complex, alkali metal-hexahydroxyplatinate (IV) complexes, tetraalkylammoniumhexahydroxyplatinate (IV) complexes, platinum (II) acetylacetanoate, platinum (II) oxalate, diamine-platinum (II) nitrite, potassium-platinum (II) nitrite, potassium platinum (II) oxalate and chloride-containing compounds such as platinum (IV) chloride, platinum (II) chloride, ethanolamine-platinum (IV) chloride complex, potassium or sodium or ammonium tetrachloroplatinate (II), tetraamine platinum (II) chloride and diamine Pt(II)dichloride, among others. Some preferred compounds include platinum (II)dinitrate, platinum (IV) chloride, and potassium or sodium tetrachloroplatinate (II). The platinum precursor solutions can optionally be stabilized by mineral acids, ammonia, alkali metal solutions such as NaOH, alkali metal salts such as NaCl, ethanolamine or carboxylic acids such as glycolic acid or oxalic acid.

The rhodium component of the catalysts of the present invention is typically added to the support as a solution of a soluble precursor or as a colloid. Rhodium-containing compounds useful in the present invention include ammonium hexachlororhodate (III), alkali metal-hexachlororhodate (III), hexaaminerhodium (III) hydroxide, hexaaminerhodium (III) chloride, rhodium sesquioxide hydrate, rhodium (III) acetylacetanoate, rhodium trinitrate, rhodium (III) trichloride, rhodium (III)acetate, and ethanolamine rhodium (II)acetate. Some preferred compounds include rhodium (III)trichloride and rhodium (III)trinitrate.

The order of addition of the metal precursors in combination with the support material is not believed to be critical. Those of ordinary skill in the art will recognize that the metal-containing components can be combined with the support material sequentially (separate fix) or simultaneously (single fix). And, as described above, among other useful processes, the metal deposition can be accomplished by wet chemical impregnation techniques and/or by physical coating (for example, spraying of aerosols onto tumbling pellets). The temperature(s) at which metal precursor deposition takes place can range from at or below ambient up to about 120° C. depending upon the deposition process selected, and those of ordinary skill in the art may readily select the appropriate deposition process and conditions to effectuate the deposition of the metal-containing compounds onto (and into) the support.

After the addition of the metal-containing compounds to the support, the metal-containing catalyst precursor may be dried. Drying may be conducted at ambient temperature or at an elevated temperature up to about 120° C. Preferably, drying is conducted at a temperature in the range of about 40° C. to about 90° C. and more preferably at a temperature at least about 60° C. The drying step may be conducted for a period of time ranging from about a few minutes to a few days. Typically, the drying time is in the range of about 6 hours to about 24 hours. Drying of the catalyst precursor can be conducted, for example, on a band dryer, in a direct fired rotary oven, or in an indirect fired rotary oven. When using physical coating for the metal deposition, drying may be done simultaneously with the coating step in the coating chamber. After deposition of the metal precursors an auxiliary chemical agent (e.g. precipitation agent) may be added, either before and/or after drying, to convert the precursors into more easily reducible or thermally decomposable forms.

After drying, the support having the precursor compound deposited thereon and, possibly, therein is typically subjected to at least one thermal treatment, under oxidative (calcination), inert (nitrogen, argon) and/or reductive (gas phase or liquid phase reductants) conditions, as is necessary for the metals of the catalyst, in order to convert the platinum and rhodium deposited thereon to Pt(0) and Rh(0). In some embodiments, the catalysts may be calcined and then the metal may be further reduced to Pt(0) and Rh(0) in-situ (i.e., in the reactor). In the case of platinum, the platinum of the compound is reducible to Pt(0) upon thermal treatment regardless of whether the atmosphere is oxidizing, inert or reducing. Thus, thermal treatment(s) may, for example, be conducted in air. Preferably, the substantial decomposition of the Pt precursor occurs during calcination and at least a portion of the platinum is converted to Pt(0). In the case of rhodium, the rhodium is preferably reduced to Rh(0) under reducing atmosphere conditions. Therefore, in various embodiments, the thermal treatment(s) is (are) conducted under a hydrogen gas containing atmosphere; alternatively, a liquid reducing agent may be employed to reduce the metals to platinum(0) and rhodium(0) on the support: for example, hydrazine, formaldehyde, formic acid, sodium formate or sodium hypophosphite may be employed to effect the requisite reduction.

The temperature(s) at which the calcination treatment(s) is (are) conducted generally range from about 150° C. to about 600° C. More typically, the temperature(s) of the thermal treatment(s) range from about 200° C. to about 550° C. The thermal treatment is typically conducted for a period of time ranging from about 1 hour to about 16 hours. More typically, the treatment is conducted for a period of time ranging from about 2 hours to about 12 hours. For example, at a thermal treatment temperature of about 350° C., the time of the treatment at temperature is in the range of about 2 hours to about 6 hours.

When a thermal treatment is conducted under a hydrogen gas-containing atmosphere—a reducing atmosphere—the thermal treatment under such gas phase reductive conditions is generally conducted at a temperature range from about 100° C. to about 500° C. When the thermal treatment is conducted in the presence of a liquid phase reducing agent, the thermal treatment under liquid phase reductive conditions is conducted at a temperature range from about 20° C. to about 95° C. It should be understood that a thermal treatment under reductive conditions can optionally be conducted in situ in a chemical reactor prior to the use of the catalyst given the reaction temperatures typically employed, for example, in the production of an adipic acid product from glucaric acid substrate. In various embodiments, a thermal treatment under reducing conditions can be conducted subsequent to a calcination treatment.

Optionally, a washing step can be employed after a thermal treatment to remove non-decomposable counterion(s) of the metal precursor compounds, such as Na, K, Cl. Typical wash solutions can include, for example, water, alcohols, polyols, carboxylic acids, or mixtures thereof. The wash solution may optionally contain a chemical reagent that will complex the counterion(s).

Figure 1:
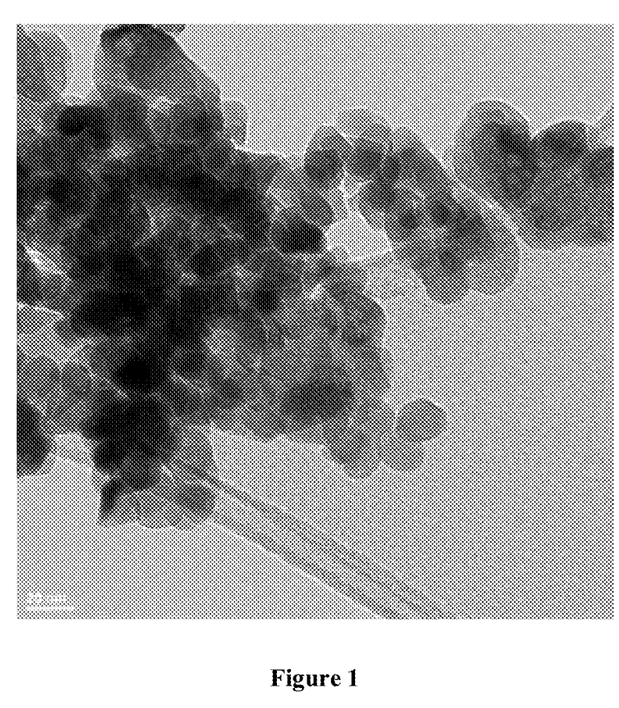
FIG. 1 is a TEM photograph of an example of a fresh catalyst prepared in accordance with the present invention comprising 0.6 wt % platinum and 0.2 wt % rhodium on a zirconia support wherein at least about 50% of the particle sizes of the metal particles are in the range of about 5-20 nm (magnification 88k×).
Figure 2:
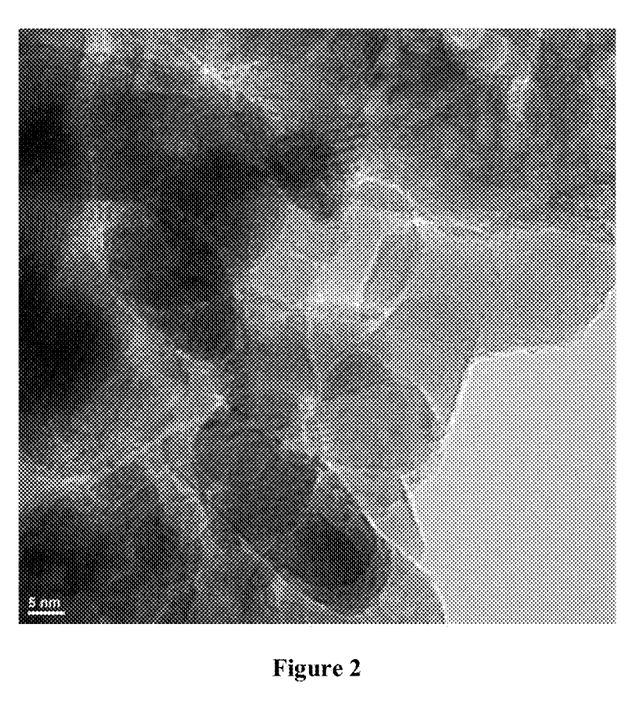
FIG. 2 is a TEM photograph of an example of a fresh catalyst prepared in accordance with the present invention comprising 0.6 wt % platinum and 0.2 wt % rhodium on a zirconia support wherein at least about 50% of the particle sizes of the metal particles are in the range of about 5-10 nm (magnification 255k×).

The reduced metals deposited on the outer surfaces of the support are in the form of metallic particles: that is to say, the platinum on the fresh catalyst exists substantially as particles of substantially platinum (0) and the rhodium on the fresh catalyst exists substantially as particles of rhodium (0). We have discovered that, although the particles sizes vary, the metallic particles of the catalysts of the present invention are substantially of a size in the range of at least about 1 nanometer (nm) and less than or equal to about 30 nanometers (nm). By "size" we mean the largest, straight line dimension of the particle. By "substantially" we mean at least about 50%. More typically, the particles are substantially of a size equal to or less than about 20 nm and, preferably, in the range of about 2 nm to about 20 nm (See, for example, the fresh catalyst photograph of FIG. 1). More preferably, the particles are at least substantially in the range of about 2 nm to about 12 nm as, for example, shown in the photograph of FIG. 2.

It should be understood that if one elects to undertake the reduction, in whole or in part, of the metals to the metal zero state in the reactor, the catalyst of the present invention is considered to be that catalyst which is intended to perform the reaction for which it was intended after any ramp up conditions which may be employed in catalytic reactions of this type.

The platinum to rhodium molar ratio of the catalyst of the present invention is in the range of from about 3:1 to about 1:2. Preferably, the platinum to rhodium molar ratio may vary, for example, from about 3:1 to about 1:1.

In some embodiments, a third metal (M3) may be added to produce a Pt/Rh/M3 catalyst wherein the M3 metal is not platinum or rhodium. In yet other embodiments a fourth metal (M4) may be added to produce a Pt/Rh/M3/M4 catalyst wherein the M4 metal is not platinum or rhodium and also not the same metal as the M3 metal. The M3 metal and M4 metal may each be selected from group of palladium, ruthenium, iridium, gold, molybdenum, tungsten, niobium, tantalum, rhenium, and osmium. More preferably the M3 metal and M4 metal are selected from palladium, molybdenum and tungsten.

The total metal loading on the final catalyst (i.e., excluding any metal originating as a constituent of the support) is equal to or less than about 10 wt % of the total catalyst weight. Generally, the total metal loading is in the range of from about 0.2 wt % to about 4 wt %. We have discovered that metal loadings in the range of about 2 wt % or less are very effective in converting the substrates disclosed herein to the desired products. In various embodiments, metal loadings in the range of from about 0.2 wt % to about 1.5 wt % are particularly effective. Thus, in various preferred embodiments the catalysts comprise platinum in an amount up to about 1.4 wt % and rhodium in an amount up to about 0.8 wt %, and in various more preferred embodiments Pt is present in an amount in the range of from about 0.4 wt % to about 1.4 wt % and Rh is present in an amount in the range of from about 0.1 wt % to about 0.8 wt %.

The catalysts of the present invention are unexpectedly and particularly effective for the hydrodeoxygenation of compositions of the general formula $ROOC(CX)_yCOOR$, where "y" is at least 2, "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl or a mono- or di-lactone thereof, to the corresponding dicarboxylic acids and derivative thereof having the general formula $ROOC(CH)_yCOOR$, where "y" is at least 2 and each "R" is, independently, selected from the group of salt-forming ions, hydrogen and hydrocarbyl or substituted hydrocarbyl or a mono- or di-lactone thereof. More particularly, glucaric acid and glucarolactones are, for example, effectively converted to adipic acid in high yield by reacting the same in the presence of hydrogen and a source of halide.

In general, the reaction can be conducted in a batch, semi-batch, or continuous reactor design using fixed bed reactors, trickle bed reactors, slurry phase reactors, moving bed reactors, or any other design that allows for heterogeneous catalytic reactions. Examples of reactors can be seen in *Chemical Process Equipment—Selection and Design*, Couper et al., Elsevier 1990, which is incorporated herein by reference. It should be understood that the substrate, hydrogen, any solvent, and the catalyst may be introduced into a suitable reactor separately or in various combinations.

As used herein, the term "hydrocarbyl" refers to hydrocarbyl moieties, preferably containing 1 to about 50 carbon atoms, preferably 1 to about 30 carbon atoms, and even more preferably 1 to about 18 carbon atoms, including branched or unbranched, and saturated or unsaturated species. Preferred hydrocarbyl can be selected from the group consisting of alkyl, alkylene, alkoxy, alkylamino, thioalkyl, haloalkyl, cycloalkyl, cycloalkylalkyl, heterocyclyl, N-heterocyclyl, heterocyclylalkyl, aryl, aralkyl heteroaryl, N-heteroaryl, heteroarylalkyl, and the like. A hydrocarbyl may be optionally substituted hydrocarbyl. Hence, various hydrocarbyls can be further selected from substituted alkyl, substituted cycloalkyl and the like.

Salt forming ions include, without limitation, for example ammonium ions and metal ions (e.g., alkali and alkaline earth metals). When R is a salt forming ion (i.e., a cation), the carboxyl group may be considered to be an anion (i.e., carboxylate anion).

In various embodiments, the hydrodeoxygenation substrate comprises a five or six carbon compound, wherein X is hydroxyl and R is independently a salt-forming ion, hydrogen, hydrocarbyl, or substituted hydrocarbyl. When, for example, the hydrodeoxygenation substrate is a six carbon chain it has four chiral centers. As a result several stereoisomers are possible.

The hydrodeoxygenation substrate may comprise various ketones. Ketones such as 2-keto-glucaric acid (2,3,4-trihydroxy-5-oxohexanedioic acid) and 3-keto-glucaric acid (2,3,5-trihydroxy-4-oxohexanedioic acid) are examples thereof.

The hydrodeoxygenation substrate may comprise various lactones which, in many embodiments are present in combination with glucaric acid. For example, not wishing to be bound by theory, it is believed that various mono- and di-lactones are present in equilibrium with glucaric acid in aqueous solution, including for example, D-glucaro-1,4-lactone, D-glucaro-6,3-lactone, and D-glucaro-1,4:6,3-dilactone. Moreover, processes have been developed to quantitatively convert glucaric acid or a salt thereof in solution to one or more lactones and recover a substantially pure lactone stream. For example see "Convenient Large-Scale Synthesis of D-Glucaro-1,4:6,3-dilactone" Gehret et al., J. Org. Chem., 74 (21), pp. 8373-8376 (2009). Also, lactones such as L-threo-4-deoxy-hex-4-enaro-6,3-lactone and L-erythro-4-deoxy-hex-4-enaro-6,3-lactone may form from the thermal decomposition of D-Glucaro-1,4:6,3-dilactone. Therefore, in various embodiments, the hydrodeoxygenation substrate comprises D-glucaro-1,4-lactone. In these and other embodiments, the hydrodeoxygenation substrate comprises D-glucaro-6,3-lactone. Still further, in these and other embodiments, the hydrodeoxygenation substrate comprises D-glucaro-1,4:6,3-dilactone. In these and other embodiments, the hydrodeoxygenation substrate comprises L-threo-4-deoxy-hex-4-enaro-6,3-lactone. Still even further, in these and other embodiments, the hydrodeoxygenation substrate comprises L-erythro-4-deoxy-hex-4-enaro-6,3-lactone.

In accordance with certain embodiments of the present invention, an adipic acid product (formula II) may be prepared by reacting, in the presence of a catalyst of the present invention, a halogen source, a hydrodeoxygenation substrate of formula I and hydrogen, according to the following reaction:

wherein X and R are defined as described above.

In preferred embodiments, the adipic acid product of formula II comprises adipic acid.

In the above reaction, a hydrodeoxygenation substrate is converted to an adipic acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

The halogen source may be in a form selected from the group consisting of atomic, ionic, molecular, and mixtures thereof. Halogen sources include hydrohalic acids (e.g., HCl, HBr, HI and mixtures thereof; preferably HBr and/or HI), halide salts, (substituted or unsubstituted) alkyl halides, or elemental halogens (e.g. chlorine, bromine, iodine or mixtures thereof; preferably bromine and/or iodine). In various embodiments the halogen source is in molecular form and, more preferably, is bromine. In more preferred embodiments, the halogen source is a hydrohalic acid, in particular hydrogen bromide.

Generally, the molar ratio of halogen to the hydrodeoxygenation substrate is about equal to or less than about 1. In various embodiments, the mole ratio of halogen to the hydrodeoxygenation substrate is typically from about 1:1 to about 0.1:1, more typically from about 0.7:1 to about 0.3:1, and still more typically about 0.5:1.

Generally, the reaction allows for recovery of the halogen source and catalytic quantities (where molar ratio of halogen to the hydrodeoxygenation substrate is less than about 1) of halogen can be used, recovered and recycled for continued use as a halogen source.

Generally, the temperature of the hydrodeoxygenation reaction mixture is at least about 20° C., typically at least about 80° C., and more typically at least about 100° C. In various embodiments, the temperature of the hydrodeoxygenation reaction is conducted in the range of from about 20° C. to about 250° C., from about 80° C. to about 200° C., more preferably from about 120° C. to about 180° C., and still more preferably between about 140° C. and 180° C. Typically, the partial pressure of hydrogen is at least about 25 psia (172 kPa), more typically at least about 200 psia (1379 kPa) or at least about 400 psia (2758 kPa). In various embodiments, the partial pressure of hydrogen is from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction is typically conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

An adipic acid product may be recovered from the hydrodeoxygenation reaction mixture by one or more conventional methods known in the art including, for example, solvent extraction, crystallization or evaporative processes.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

General Description of the Synthesis of the Exemplified Pt/Rh Catalysts (by Incipient Wetness Impregnation)

An aqueous solution of a platinum precursor compound and rhodium precursor compound was added to supports of zirconia, titania, silica, carbon, zeolite and montmorillonite in the form of particles (Examples 1-4) and extrudate (Example 5) in multiple portions. The metal precursor solution was either pipetted or sprayed onto the support for the impregnation. Each mixture was agitated to evenly impregnate the support. Each sample was dried in a 60° C. oven or at room temperature overnight under a dry air purge. Each sample was then reduced under forming gas (5% $H_2$ and 95% $N_2$) atmosphere typically at 350° C. for 6 hours with 2° C./min temperature ramp rate. By adjusting the concentrations of the solutions of the platinum and rhodium precursor compounds, a series of catalysts with various metal loadings and molar ratios of Rh and Pt were prepared.

As illustrated in the examples to follow, different metal precursor compounds can be used to prepare catalysts with various Rh and Pt metal loadings and molar ratios of Rh and Pt on different supports. When the Rh and Pt precursor compounds were found to be incompatible (meaning formation of precipitate upon contact of solutions), one metal precursor solution was added to the support to impregnate the support with one metal, followed by drying in a 60° C. oven or at room temperature overnight under a dry air purge, and subsequent addition of the other metal precursor solution was undertaken to impregnate the single metal containing support with the other metal. The material was further dried in a 60° C. oven or at room temperature overnight under a dry air purge.

Example 1

Synthesis of Pt/Rh Zirconia Catalyst by Incipient Wetness Impregnation (Single Fix)

An aqueous solution of platinum nitrate and rhodium nitrate (20 ml in total volume containing 0.41 g Rh and 1.17 g Pt) was added to a zirconia support (100 g, 90-180 μm particle size) in multiple portions using a pipette over a period of 10 min. During the addition of the solution, the mixture was agitated to evenly impregnate the support. The sample was dried in a 60° C. oven overnight under a dry air purge. The sample was then reduced under forming gas (5% $H_2$ and 95% $N_2$) atmosphere at 350° C. for 6 hours with 2° C./min temperature ramp rate. The final catalyst contained 0.41 wt % Rh and 1.17 wt % Pt.

Example 2

Synthesis of Pt/Rh Zirconia Catalyst by Incipient Wetness Impregnation (Separate Fix)

An aqueous solution of $(NH_3)_6Rh(OH)_3$ (10 ml in total volume containing 0.12 g Rh) was added to a zirconia support (50 g, 90-180 μm particle size) in multiple portions using a pipette over a period of 5 min. During addition of the solution, the mixture was agitated to evenly impregnate the support. The sample was dried in a 60° C. oven overnight under a dry air purge and then cooled to room temperature. To this material, an aqueous solution of platinum nitrate (10 ml in total volume containing 0.27 g Pt) was added in multiple portions using a pipette over a period of 5 min. During addition of the solution, the mixture was agitated to evenly impregnate the support. The sample was dried in a 60° C. oven overnight under a dry air purge. The sample was then reduced under forming gas (5% $H_2$ and 95% $N_2$) atmosphere at 350° C. for 6 hours with 2° C./min temperature ramp rate. The final catalyst contained 0.24 wt % Rh and 0.54 wt % Pt.

Example 3

Use of Pt/Rh Catalysts for Selective Hydrodeoxygenation of Glucaric Acid Monolactone in a Batch Reactor Catalyst (20 mg) produced in accordance with the general description set forth hereinabove was weighed into a glass vial insert, followed by addition of a solution (100 1l in total volume) containing glucaric acid monolactone (0.8 M) and HBr (0.6 M) in acetic acid. The glass vial insert was loaded into a pressure reactor and the reactor was closed. The atmosphere in reactor was replaced with hydrogen and pressurized to 900 psig at room temperature. Reactor was heated to 160° C. and maintained at 160° C. for 1.5 hours with orbital shaking. After 1.5 hours, the shaking was stopped and reactor was cooled to 40° C. Pressure in reactor was then slowly released. The glass vial insert was removed from reactor and centrifuged. The clear solution was diluted with deionized water and analyzed by Fast-MS (with deuterated adipic acid d-8 as internal standard) and HPLC to determine the yield of adipic acid. A selection of results is shown in Table 1. Weight percentages of metals are nominal weight % on a total catalyst weight basis.

TABLE 1

| Entry | Support Type | Surface Area ($m^2/g$) | Average Pore Diameter (nm) | Pore Volume (ml/g) | Rh wt % | Pt wt % | Adipic Acid Yield (%) |
|---|---|---|---|---|---|---|---|
| 1 | $ZrO_2$ | 36 | 14 | 0.18 | 0.82 | 2.34 | 93 |
| 2 | $ZrO_2$ | 36 | 14 | 0.18 | 0.25 | 0.75 | 92 |
| 3 | $ZrO_2$ | 32 | 16 | 0.16 | 0.41 | 1.17 | 83 |
| 4 | $ZrO_2$ | 32 | 17 | 0.17 | 0.41 | 1.17 | 97 |
| 5 | $ZrO_2$ | 46 | 11 | 0.14 | 0.29 | 0.82 | 93 |
| 6 | $ZrO_2$ | 36 | 13 | 0.10 | 0.08 | 0.44 | 83 |
| 7 | $ZrO_2$ | 44 | 13 | 0.20 | 0.29 | 0.82 | 93 |
| 8 | $ZrO_2$ | 44 | 13 | 0.20 | 0.36 | 1.27 | 85 |

TABLE 1-continued

| Entry | Support Type | Surface Area (m²/g) | Average Pore Diameter (nm) | Pore Volume (ml/g) | Rh wt % | Pt wt % | Adipic Acid Yield (%) |
|---|---|---|---|---|---|---|---|
| 9 | ZrO$_2$ | 43 | 16 | 0.21 | 0.29 | 0.82 | 98 |
| 10 | ZrO$_2$ | 43 | 16 | 0.21 | 0.40 | 0.61 | 98 |
| 11 | ZrO$_2$ (5% SiO$_2$) | 83 | 8 | 0.22 | 0.29 | 0.82 | 96 |
| 12 | ZrO$_2$ (12% La$_2$O$_3$) | 92 | 5 | 0.16 | 0.31 | 1.37 | 82 |
| 13 | ZrO$_2$ | 114 | 8 | 0.33 | 0.46 | 1.07 | 95 |
| 14 | ZrO$_2$ | 114 | 8 | 0.33 | 0.31 | 1.37 | 82 |
| 15 | ZrO$_2$ (7% Y$_2$O$_3$) | 103 | 5 | 0.18 | 0.31 | 1.37 | 89 |
| 16 | ZrO$_2$ (7% Y$_2$O$_3$) | 103 | 5 | 0.18 | 0.46 | 1.07 | 87 |
| 17 | Silica | 799 | 8 | 0.15 | 1.03 | 1.95 | 28 |
| 18 | Silica | 799 | 8 | 0.15 | 1.29 | 1.46 | 26 |
| 19 | Silica | 287 | 13 | 1.25 | 1.03 | 1.95 | 19 |
| 20 | Silica | 287 | 13 | 1.25 | 0.80 | 2.43 | 14 |
| 21 | Silica | 498 | 7 | 0.88 | 0.41 | 1.17 | 40 |
| 22 | Zeolite | 399 | 9 | 0.12 | 0.46 | 1.07 | 18 |
| 23 | Zeolite | 399 | 9 | 0.12 | 0.36 | 1.27 | 9 |
| 24 | Zeolite | 518 | 7 | 0.24 | 0.46 | 1.07 | 16 |
| 25 | Zeolite | 518 | 7 | 0.24 | 0.31 | 1.37 | 13 |
| 26 | Carbon | 166 | 22 | 0.98 | 1.03 | 1.95 | 72 |
| 27 | Carbon | 166 | 22 | 0.98 | 0.62 | 2.73 | 70 |
| 28 | Carbon | 166 | 22 | 0.98 | 0.52 | 1.36 | 20 |
| 29 | Carbon | 166 | 22 | 0.98 | 0.31 | 1.87 | 19 |
| 30 | Carbon | 1323 | 6 | 0.13 | 1.03 | 1.95 | 18 |
| 31 | Carbon | 1323 | 6 | 0.13 | 0.62 | 2.73 | 13 |
| 32 | Carbon | 859 | 8 | 0.19 | 1.03 | 1.95 | 48 |
| 33 | Carbon | 859 | 8 | 0.19 | 0.62 | 2.73 | 40 |
| 34 | Montmorillonite | 210 | 6 | 0.38 | 1.03 | 1.95 | 74 |
| 35 | Montmorillonite | 210 | 6 | 0.38 | 0.62 | 2.73 | 70 |
| 36 | Montmorillonite | 313 | 6 | 0.42 | 1.03 | 1.95 | 70 |
| 37 | Montmorillonite | 313 | 6 | 0.42 | 0.62 | 2.73 | 63 |
| 38 | Titania | 49 | 19 | 0.19 | 0.62 | 2.73 | 87 |
| 39 | Titania | 50 | 27 | 0.27 | 1.03 | 1.95 | 89 |

Example 4

Synthesis and Testing of Pt/Rh Zirconia and Pt/Rh Titania Catalysts in a Flow Reactor Pt/Rh zirconia and Pt/Rh titania catalysts were prepared in accordance with the previous examples and tested for selective hydrodeoxygenation of glucaric acid monolactone in a continuous flow fixed bed reactor over a period of 100 hours. The Pt/Rh zirconia catalyst was effective for the selective hydrodeoxygenation of glucaric acid monolactone without any appreciable loss of catalyst activity during the 100 hour test. The Pt/Rh titania catalyst showed an appreciable loss of activity during the 100 hour test.

Example 5

Synthesis and Testing of a Pt/Rh Zirconia Extrudate Catalyst in a Flow Reactor

An aqueous solution of platinum nitrate and rhodium nitrate (20 ml in total volume containing 0.20 g Rh and 0.60 g Pt) was sprayed onto a zirconia support (100 g, 1.5×1.5 mm extrudate) over a period of 20 min. During addition of solution, the mixture was agitated to evenly impregnate the support. The sample was dried at room temperature overnight under a dry air purge in a 500 ml round bottom flask on a rotary evaporator with gentle tumbling. The sample was then reduced under forming gas (5% H$_2$ and 95% N$_2$) atmosphere at 350° C. for 6 hours with 2° C./min temperature ramp rate. The final catalyst contained 0.20 wt % Rh and 0.60 wt % Pt located in a shell on the surface of the extrudate. This catalyst was effective for the selective hydrodeoxygenation of glucaric acid monolactone in a continuous flow fixed bed reactor over a period of 1000 hours without any appreciable loss of catalyst activity.

We claim:

1. A heterogeneous catalyst comprising platinum and rhodium on a support selected from the group consisting of a zirconia support comprised of zirconia and no more than about 5 wt % of other materials, a stabilized (doped) zirconia support comprised of zirconia and between about 1 wt % and about 40 wt % of dopants, and mixtures thereof, wherein: (a) the molar ratio of platinum to rhodium is in the range of from about 3:1 to about 1:2, (b) platinum is present in an amount in the range of from about 0.4 wt % to about 1.4 wt %, (c) rhodium is present in an amount in the range of from about 0.1 Wt % to about 0.8 wt %, and (d) the average pore diameter of the support is in the range of from about 5 nm to about 70 nm.

2. The catalyst of claim 1, wherein the surface area of the catalyst is equal to or less than about 60 m²/g.

3. The catalyst of claim 1, wherein the surface area of the support is in the range of between about 15 m²/g and about 125 m²/g.

4. The catalyst of claim 3, wherein the support is the zirconia support comprised of zirconia and no more than about 5 wt % of other materials.

5. The catalyst of claim 3, wherein the catalyst further comprises a metal selected from the group of palladium, molybdenum and tungsten.

6. The catalyst of claim 1, wherein at least a portion of the platinum is present as Pt(0).

7. The catalyst of claim 6, wherein at least a portion of the rhodium is present as Rh(0).

8. The catalyst of claim 1, wherein the catalyst further comprises a metal selected from the group of palladium, molybdenum and tungsten.

9. The catalyst of claim 1, wherein the support is the zirconia support comprised of zirconia and no more than about 5 wt % of other materials.

10. The catalyst of claim 1, wherein the particle sizes of the platinum and rhodium metals are substantially in the range of from about 2 nm to about 20 nm.

11. A process for producing an adipic acid product comprising reacting a substrate of formula I or a mono- or di-lactone thereof:

where each "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl, with hydrogen in the presence of the heterogeneous catalyst of claim 3, to convert the substrate to the adipic acid product of formula II where R is as defined above for formula I.

12. The process of claim 11, wherein the support is the zirconia support comprised of zirconia and no more than about 5 wt % of other materials.

13. The process of claim 11, wherein the average pore diameter of the support is in the range of from about 5 nm to about 40 nm.

14. The process of claim 11, wherein the surface area of the support is in the range of between about 15 m$^2$/g and about 125 m$^2$/g.

15. The process of claim 11, wherein at least a portion of the platinum is present as Pt(0).

16. The process of claim 15, wherein at least a portion of the rhodium is present as Rh(0).

17. The process of claim 11, wherein the particle sizes of the platinum and rhodium metals are substantially in the range of from about 2 nm to about 30 nm.

18. process of claim 11, wherein the particle sizes of the platinum and rhodium metals are substantially in the range of from about 2 nm to about 20 nm.

19. The process of claim 11, wherein the yield of adipic acid is at least 80%.

20. The process of claim 11, wherein the adipic acid product comprises adipic acid.

21. The process of claim 11, wherein each "R" is independently hydrogen, a salt forming ion, or an unsubstituted hydrocarbyl having from 1 to 18 carbon atoms.

22. The process of claim 21, wherein each "R" is independently hydrogen or a salt forming ion selected from the group consisting of ammonium ions, alkali metal ions, and alkaline earth metal ions.

23. The process of claim 22, wherein each "X" is hydroxyl.

24. The process of claim 23, wherein the substrate of formula I or mono- or di-lactone thereof is reacted with hydrogen in the presence of the catalyst and a halogen source.

25. The process of claim 24, wherein the halogen source comprises as hydrohalic acid.

26. A heterogeneous catalyst comprising platinum and rhodium on a support selected from the group consisting of a zirconia support comprised of zirconia and no more than about 5 wt % of other materials, a stabilized (doped) zirconia support comprised of zirconia and between about 1 wt % and about 40 wt % of dopants, and mixtures thereof, wherein: (a) the molar ratio of platinum to rhodium is in the range of from about 3:1 to about 1:2, (b) platinum is present in an amount in the range of from about 0.4 wt % to about 1.4 wt %, (c) rhodium is present in an amount in the range of from about 0.1 wt % to about 0.8 wt %, and (d) the particle sizes of the platinum and rhodium metals are substantially in the range of from about 2 nm to about 30 nm.

27. The catalyst of claim 26, wherein the particle sizes of the platinum and rhodium metals are substantially in the range of from about 2 nm to about 20 nm.

28. The catalyst of claim 26, wherein the particle sizes of the platinum and rhodium metals are substantially in the range of from about 2 nm to about 12 nm.

29. The catalyst of claim 26, wherein the support is the zirconia support comprised of zirconia and no more than about 5 wt % of other materials.

30. The catalyst of claim 26, wherein the surface area of the catalyst is equal to or less than about 60 m$^2$/g.

31. The catalyst of claim 26, wherein the surface area of the support is in the range of between about 15 m$^2$/g and about 125 m$^2$/g.

32. The catalyst of claim 26, wherein the average pore diameter of the support is in the range of from about 5nm to about 70 nm.

33. The catalyst of claim 26, wherein the catalyst further comprises a metal selected from the group of palladium, molybdenum and tungsten.

34. A process for producing an adipic acid product comprising reacting a substrate of formula I or a mono- or di-lactone thereof:

where each "X" is, independently, selected from the group of hydroxyl, oxo, halo, acyloxy and hydrogen provided that at least one X is not hydrogen, and each "R" is, independently, selected from the group of salt-forming ions, hydrogen and hydrocarbyl or substituted hydrocarbyl, with hydrogen in the presence of the heterogeneous catalyst of claim 9, to convert the substrate to the adipic acid product of formula II where R is as defined above for formula I.

35. The process of claim 34, wherein the support is the zirconia support comprised of zirconia and no more than about 5 wt % of other materials.

36. The process of claim 34, wherein the average pore diameter of the support is in the range of from about 5 nm to about 70 nm.

37. The process of claim 34, wherein the surface area of the support is in the range of between about 15 m$^2$/g and about 125 m$^2$/g.

38. The process of claim 34, wherein at least a portion of the platinum is present as Pt(0).

39. The process of claim 38, wherein at least a portion of the rhodium is present as Rh(0).

40. The process of claim 34, wherein the particle sizes of the platinum and rhodium metals are substantially in the range of from about 2 nm to about 20 nm.

41. The process of claim 34, wherein the yield of adipic acid is at least 80%.

42. The process of claim 34, wherein the adipic acid product comprises adipic acid.

43. The process of claim 34, wherein each "R" is independently hydrogen, a salt forming ion, or an unsubstituted hydrocarbyl having from 1 to 18 carbon atoms.

44. The process of claim 43, wherein each "R" is independently hydrogen or a salt forming ion selected from the group consisting of ammonium ions, alkali metal ions, and alkaline earth metal ions.

45. The process of claim 44, wherein each "X" is hydroxyl.

46. The process of claim 45, wherein the substrate of formula I or mono- or di-lactone thereof is reacted with hydrogen in the presence of the catalyst and a halogen source.

47. The process of claim 46, wherein the halogen source comprises as hydrohalic acid.

* * * * *